Figure 1:
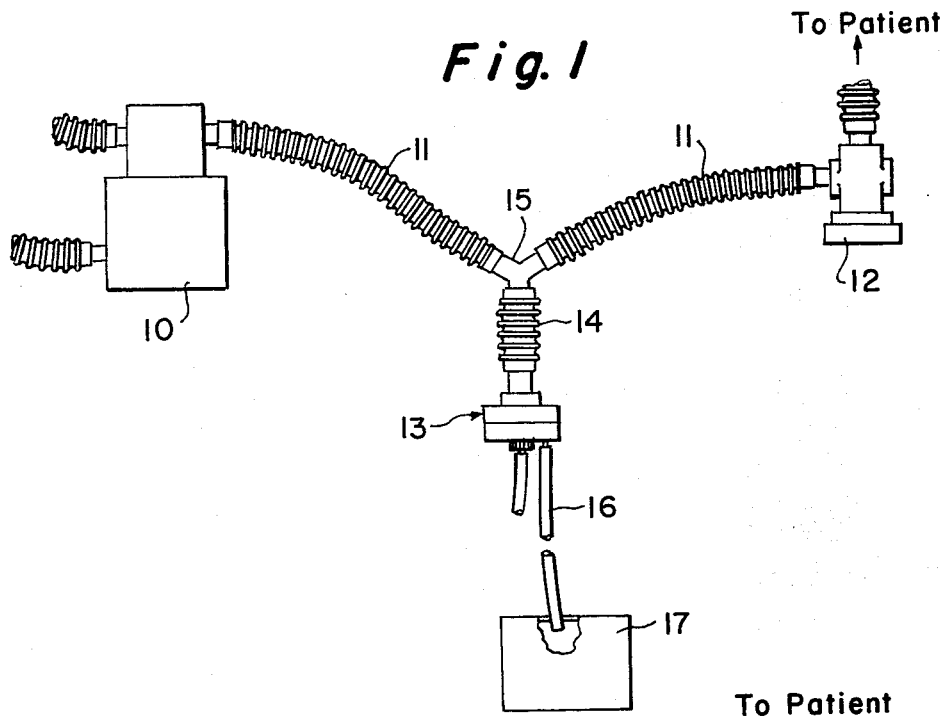

United States Patent
Eross

[11] 3,968,812
[45] July 13, 1976

[54] APPARATUS FOR REMOVAL OF CONDENSED MOISTURE FROM RESPIRATORY TUBES

[75] Inventor: Bela Eross, Penn Hills Township, Allegheny County, Pa.

[73] Assignee: Instrumentation Industries, Inc., Pittsburgh, Pa.

[22] Filed: Oct. 12, 1971

[21] Appl. No.: 188,093

[52] U.S. Cl. ............................ 137/188; 137/204
[51] Int. Cl.² .................................... F16T 1/14
[58] Field of Search ............ 137/204, 188, 107, 525

[56] References Cited
UNITED STATES PATENTS

| | | | |
|---|---|---|---|
| 2,496,470 | 2/1950 | Hodsdon | 137/204 |
| 2,610,645 | 9/1952 | Wagner | 137/188 |
| 2,859,764 | 11/1958 | Golay | 137/204 |
| 2,907,340 | 10/1959 | Kenney | 137/188 |
| 3,608,574 | 9/1971 | Beaussant | 137/525 |

*Primary Examiner*—Alan Cohan
*Attorney, Agent, or Firm*—Buell, Blenko & Ziesenheim

[57] ABSTRACT

The specification discloses drain valve apparatus for automatically draining condensed moisture from tubing, such as tubing connected to a respirator or nebulizer, without admitting ambient air to the tubing. One embodiment of drain valve apparatus comprises a casing of transparent plastic material having a chamber from which condensed moisture flows to atmosphere. A diaphragm valve, of the bulb-type, is biased to seated position to prevent admittance of ambient air to the tubing and opens only responsively to a certain weight of accumulated moisture active thereon to allow moisture to enter the chamber. In a second embodiment, a diaphragm valve is activated to seated position by a second bulb-type diaphragm connected thereto and subject to the pressure in the tubing. Also, a check valve prevents back flow of ambient air to the tubing under negative pressure conditions in the tubing.

11 Claims, 5 Drawing Figures

INVENTOR
Bela Eross

BY

HIS ATTORNEYS

APPARATUS FOR REMOVAL OF CONDENSED MOISTURE FROM RESPIRATORY TUBES

This invention relates to apparatus for automatically draining condensed moisture from tubing, especially tubing connected to a respirator or nebulizer such as are employed in hospitals to assist a patient in breathing.

Drainage of condensed moisture which accumulates in tubing, such as utilized communicating nebulized air or pressurized air containing oxygen to assist a hospital patient in breathing, is necessary to prevent interference with the respiration of the patient. It is common practice to open the tubing connections manually to allow the moisture to drain into a container. This practice objectionable as it interrupts the respiratory therapy and requires surveillance by personnel in order to prevent undesired accumulation of moisture.

In order to avoid the undesired interruption of respiration therapy to patients and the necessity for surveillance by personnel, I propose to provide apparatus which automatically drains condensed moisture from the tubing utilized in respiratory systems and equipment and which in no way interferes with sensitivity or patient triggering pressures during assisted respiratory ventilation.

More particularly, I propose to provide such apparatus including diaphragm-controlled valves sensitive to inhalation and exhalation pressures of the patient for controlling drainage of condensed moisture accumulation in a water trap in a manner that does not permit entry of ambient air into the tubing during the inhalation phase of the patients respiration cycle.

Figure 2:
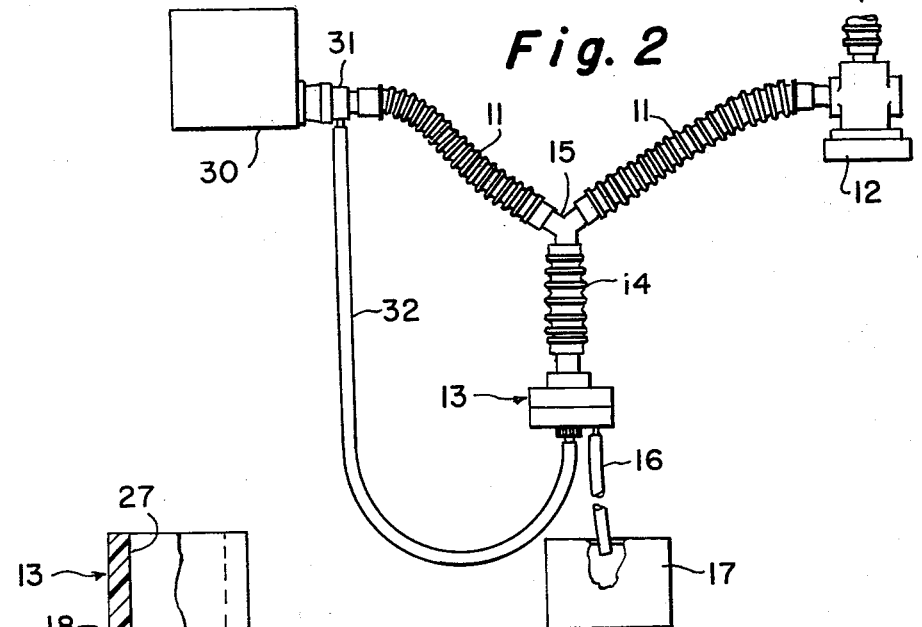
Figure 3:
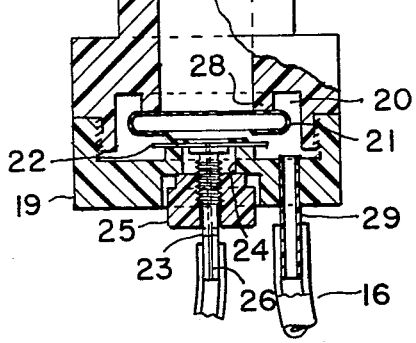
Figure 4:
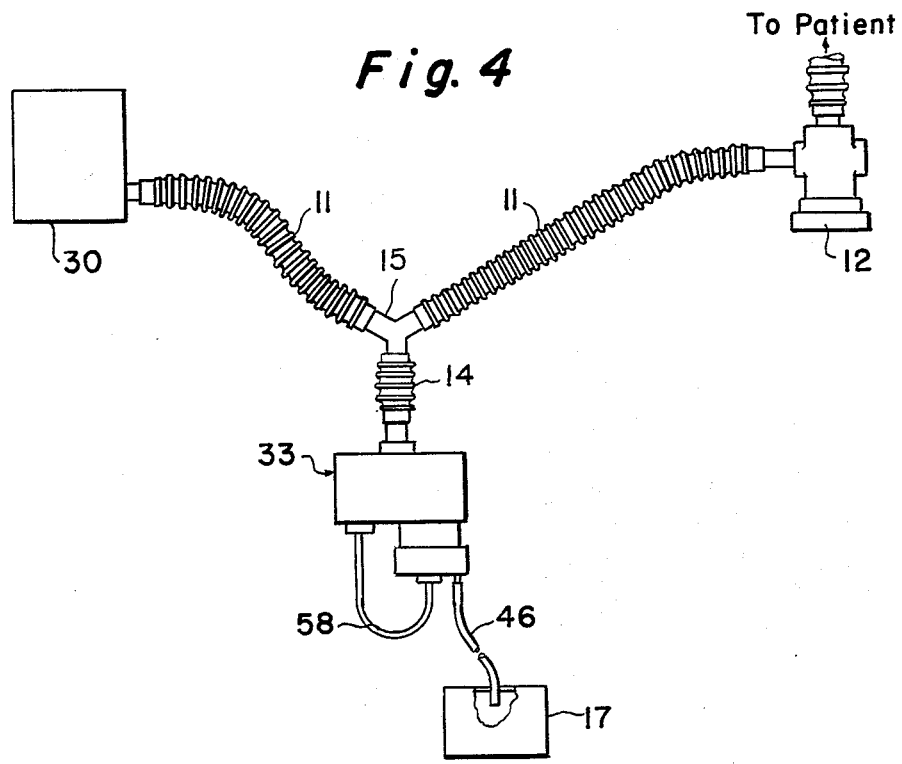
Figure 5:
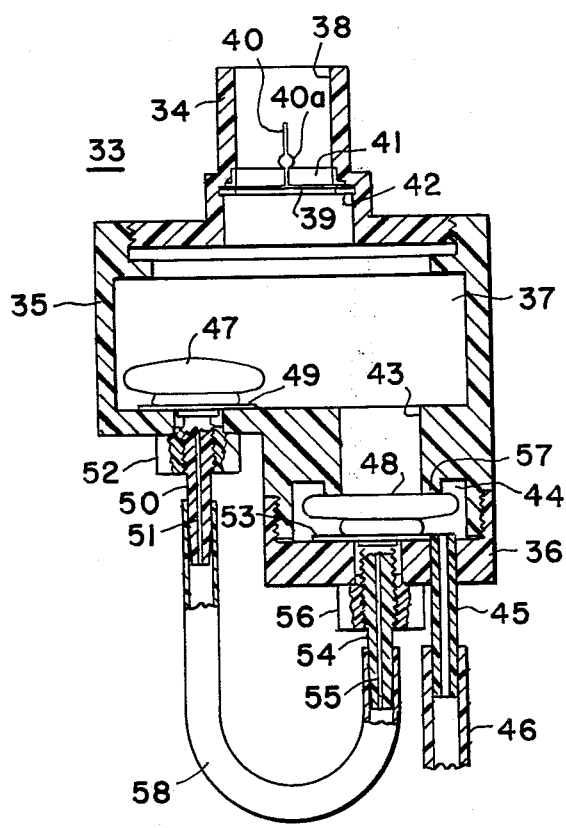

The apparatus which I propose to provide will be described hereinafter in greater detail in connection with the accompanying drawings, wherein:

FIG. 1 is a simplified view, showing use of one embodiment of my novel drainage apparatus for draining moisture from tubing of a spontaneous nebulization ventilation equipment, FIG. 2 is a simplified view, showing adaptation of the embodiment of FIG. 1, to use in a positive pressure breathing equipment, FIG. 3 is an elevational view, largely in cross-section and at full scale, showing details of the one embodiment of my novel drainage apparatus utilized in FIGS. 1 and 2, FIG. 4 is a simplified view, showing use of another embodiment of my novel drainage apparatus in connection with tubing of a positive pressure breathing equipment, and FIG. 5 is an elevational view, largely in cross-section and at full scale, of the embodiment of my novel drainage apparatus utilized in FIG. 4.

Referring to FIG. 1, the spontaneous nebulizer equipment shown comprises a conventional nebulizer 10 which supplies controlled air under natural or unassisted breathing conditions to the patient via tubing 11 and an inhalation valve 12. A novel drainage control valve or trap 13 is connected, through a short length of tube 14 and a Y-fitting 15, into the tubing 11, and through a flexible hose 16 to a container, such as a plastic type bag or envelope 17. The Y-fitting 15 is preferably located at a low point in the length of tubing 11 to insure drainage, by gravity, of moisture condensed in sections of tubing 11 at either side of the Y-fitting, to the drainage control valve 13.

As shown in FIG. 3, the drainage control valve 13 comprises a generally cylindrical casing or body, preferably of transparent light-weight plastic material, having two parts 18 and 19 screw-threadedly joined together. Formed within the valve body is a chamber 20. Contained within the chamber 20 is a hollow disc-like bulb or diaphragm 21 cemented on one side to a plate 22 to which a threaded stem 23 is fixed. Stem 23 extends through a port 24 in the wall of the body section 19 and is secured in position by a nut 25 screwed over the end of the stem. Stem 23 has a passage 26 therethrough which is open to the interior of the diaphragm and via which pressurizing vapor or air may be supplied to expand the diaphragm. As utilized in FIG. 1, however, passage 26 is allowed to remain open to ambient atmospheric pressure.

Formed in the body section 18 is a relatively large diameter bore or passage 27 in which condensed moisture may accumulate so long as the diaphragm 21 is seated on an annular valve seat 28 located at the inner or bottom end of passage 27. The section 18 has a slightly tapered sleeve-like end portion which is telescopically inserted in one end of flexible tube 14, the other end of which fits over the branch sleeve of the Y-fitting 15.

Secured, as by cementing, in a hole through the wall of section 19, is an outlet tube 29. The inner end of the tube 29 is open to chamber 20 and moisture which collects in chamber 20 is drained therefrom via the tube 29. Flexible hose 16 is connected to the outlet tube 29 and conducts the drained moisture to bag 17.

In the operation of the nebulization equipment shown in FIG. 1, nebulizer 10 simply supplies a medicated or other vapor into the air stream drawn, without assistance, by the natural inhalation of the patient, through the nebulizer 10, tube 11, and inhalation valve 12 to the patient. The inhalation valve 12 prevents back flow of air exhaled by the patient into tubing 11, and allows exhaled air to return directly to atmosphere via an exhaust port in the inhalation valve.

On inhalation by the patient through tubing 11, the differential of pressures acting on the diaphragm bulb 21 causes it to expand and seat firmly on valve seat 28, thus effectively preventing ambient air from being drawn into tubing 11 via the drain valve 13. On exhalation by the patient, the diaphragm 21 is not subject to the back pressure of air exhaled by the patient and consequently due to its normal expanded shape remains seated on the valve seat 28. In no case, therefore, is ambient air allowed to be drawn past the diaphragm 21 into tubing 11 when the patient inhales.

Now let it be assumed that condensed moisture has dripped slowly back in the two downwardly sloping sections of tubing 11, and has accumulated in the passage 27. When the weight of the accumulated moisture in passage 27 is sufficient, during a period of exhalation by the patient, to overcome the normal bias of diaphragm 21 to seated position on the valve seat 28, the accumulated moisture will drain past the unseated diaphragm 21 into chamber 20 and thence via tube 16 to bag 17.

As soon as the weight of the moisture is removed, diaphragm 21 again reseats on valve seat 28 and remains so until a sufficient time elapses to again accumulate sufficient condensed water in passage 27 to unseat the diaphragm.

Thus drain valve 13 functions automatically to drain condensed moisture from tubing 11 periodically, no surveillance by personnel being required beyond emptying the accumulated water in bag 17.

Referring now to FIG. 2, the manner in which drain valve 13 is employed in the equipment shown therein will now be described. The respiratory equipment illustrated is of the intermittent positive pressure type for patients that require pressure assistance for inhalation. The equipment differs from the nebulizer equipment, previously described, in that there is substituted for the nebulizer 10 a conventional positive pressure breathing unit 30 hereinafter referred to simply as the IPPB unit.

It will be apparent that, in view of the pressure under which air is supplied through tubing 11 to the patient during the inhalation phase of the breathing cycle, the drain valve 13 cannot be utilized, as in FIG. 1, with the interior of diaphragm 21 open to ambient atmospheric pressure, the reason being that the diaphragm 21 would be unseated during inhalation by the patient and thus allow ambient air to flow past the drain valve into the tubing and thus change the pressure condition in the tubing as well as the air-vapor constituency.

In order to adapt the drain valve 13 for use in the equipment of FIG. 2, a T-fitting 31 is interposed in the connection between the IPPB unit and tubing 11 and the branck sleeve branch the T-fitting is connected by a flexible hose 32 to the end of stem 23.

Accordingly, the pressure under which air is supplied by the IPPB unit to the patient during inhalation is also supplied via hose 32 to pressurize the diaphragm bulb 21 and firmly seat the diaphragm on the valve seat 28. Thus, inflow of ambient air into tubing 11 during the inhalation phase of the respiration cycle, is positively prevented.

During the exhalation phase of the respiration cycle, the inhalation valve 12 prevents back flow of exhaled air into tubing 11 and by-passes it directly to atmosphere at inhalation valve 12. At the same time the pressure of the air supplied by the IPPB unit is reduced to zero. Thus, during the exhalation phase of the respiration cycle of the patient, diaphragm 21 remains seated on valve seat 28 but not under inflationary pressure. In any case, ambient atmospheric air is not allowed to flow past the diaphragm into the tubing 11.

Assuming now that condensed moisture has accumulated in passage 27 and possibly also in tube 14, it will be seen that here again it is the weight of the accumulated water which will unseat the diaphragm and drain the moisture into chamber 20 and thence via hose 16 to bag 17. Also as in the FIG. 1 equipment, the drainage of water will be effected automatically and at intervals of time, during exhalation by the patient, whenever the weight of accumulated water becomes sufficient to unseat diaphragm 21.

Referring to FIG. 4, the equipment shown is similar to that of FIG. 2 except for substitution of another embodiment of drain valve 33 for the drain valve 13, which substitution eliminates the need for the T-fitting 31 and hose 32. In the equipment shown in FIG. 4, an IPPB unit 30 supplies controlled pressure air via tubing 11 and inhalation valve 12 to the patient. The drain valve 33 is connected into tubing 11 by a Y-fitting 15 as was drain valve 13 in the previously described equipment.

Referring to FIG. 5, the drain valve 33 comprises a generally cylindrical body having three sections 34, 35 and 36 suitably joined by screw-threaded connections. The sections are preferably of light-weight transparent plastic material.

Formed in section 35 is a central cylindrical chamber 37 which communicates via a coaxial bore or passage 38 in section 34 with tubing 14, in turn connected to the branch sleeve of the fitting 15.

Disposed within the passage 38 is a check valve 39, in the form of a thin rubber disc. The rubber disc has an integral coaxial rubber stem 40 which extends through a bore in a central hub of a spider disc 41 preferably of molded plastic material. The spider disc 41 is retained in a circumferential groove in the wall of section 34 by a split snapring 42 also engaged in a corresponding circumferential groove. The rubber stem 40 has a ball 43 formed therein which yields to allow the stem 40 to be inserted through the bore in the hub of the spider disc 41 and then expands to cause the check valve disc to be supported in seated relation on the lower face of the spider disc 41.

Chamber 37 also communicates via a bore or passage 43 with another cylindrical chamber 44. Cemented in a bore in the wall of section 36 is a tube 45, preferably of plastic material, by which chamber 44 communicates with a flexible hose 46 leading to a plastic bag or envelope 17.

Disposed respectively in chambers 37 and 44 are similar disc-like diaphragms 47 and 48, of the bulb type, corresponding to diaphragm 21 of the previously described embodiment of drain valve. Diaphragm 47 is bonded to a centrally perforated plate 49 to which a threaded stem 50 is fixed. Stem 50 extends through a bore in the wall of section 35 and has a passage 51 therethrough communicating through the plate 49 with the interior of the diaphragm 47. A nut 52 of plastic or rubber material, is screwed over stem 50 to secure diaphragm firmly to the wall of the section 35.

Diapghragm 48 is similarly bonded to a plate 53 and a threaded stem 54 fixed to the plate extends through a hole in the wall of section 36. Stem 54 has a central longitudinal passage 55 therethrough communicating with the interior of diaphragm 48. A nut 56 of plastic or rubber material is screwed over the stem 54 and serves to secure the diaphragm 48 firmly in position to the wall of section 36.

Body section 35 has formed thereon, at the lower end of passage 43, an annular rib 57 which serves as a valve seat for diaphragm 48.

The respective stems 50 and 54 of diaphragms 47 and 48 are connected by a flexible hose 58. The two connected diaphragms 47 and 48 thus form a closed pressure system wherein pressure exerted in chamber 37 on diaphragm 47 is transmitted via the air trapped in the diaphragms and hose 58 to diaphragm 48 to cause it to expand and firmly seat on the seat 57.

In the operation of the equipment of FIG. 4, the IPPB unit 30 supplies pressurized air via tubing 11 and inhalation valve 12 to the patient during the inhalation phase of the respiratory cycle. On exhalation by the patient, the air exhaled by the patient is by-passed by the inhalation valve 12 direct to atmosphere and back flow into tubing 11 thereby prevented.

It will be apparent that the pressure of the air supplied by the IPPB unit 30 acts to unseat the rubber check valve 39 and to charge chamber 37. Pressure in chamber 37 exerted on diaphragm 47, causes diaphragm 48 to be expanded to firmly seat on annular seat 57 against the pressure acting via passage 43 on the smaller seated area of diaphragm 48. Accordingly, ambient air is positively sealed against entry into chamber 37, passage 38 and tubing 11, notwithstanding that check valve 39 may be unseated.

When the pressure in tubing 11 is relieved during the exhalation phase of the respiratory cycle, check valve 39 seats to prevent back flow of pressurized air from chamber 37 to tubing 11. At the same time, the air pressure trapped in chamber 37 continues to act on diaphragm 47, which in turn, causes diaphragm 48 to seat firmly on annular seat 57. Thus, the inflow of ambient atmospheric air into the tubing 11 during exhalation by the patient is positively prevented, even during so-called negative pressure ventilation wherein the pressure in tubing 11 during exhalation by the patient may be less than zero. It will be apparent that, when negative pressure occurs in tubing 11, diaphragm 48 would be unseated by diminution of pressure on diaphragm 47, were it not for check valve 39 which prevents back flow of pressure from chamber 37 to passage 38 and tubing 11.

Now let it be assumed that moisture condensed in tubing 11 drains down into tubing 14 and passage 38. When check valve 39 is unseated by the build-up of pressure in tubing 11, the moisture will of course run down into chamber 37, where it accumulates, because diaphragm 48 is biased into seated position on annular valve seat 57. Whenever the weight of the water acting over the inner seated area of diaphragm 48 becomes sufficient, diaphragm 48 will be unseated from valve seat 57, thus allowing the accumulated water to drain through chamber 44, tube 45 and hose 46 to the bag 17. Should ambient atmospheric air leak past diaphragm 48 while unseated to drain moisture, check valve 39 prevents inflow through passage 38 to tubing 11.

It will thus be seen that drain valve 33 functions automatically to periodically drain accumulated moisture from tubing 11 into bag 17, from which it may be removed as the bag becomes filled.

While several specific embodiments of drain valve apparatus have been disclosed and described herein, and typical equipments referred to in which the embodiments may be employed, it should be apparent that variations in the embodiments, as described, may be made as well as in the type of equipments in which they are used, within the scope of the appended claims.

I claim:

1. Drain valve means for automatically draining condensed moisture from tubing, said valve means comprising a casing having a passage adapted to be connected to the tubing and forming an inlet chamber into which condensed moisture from the tubing may flow by gravity, an outlet chamber with which said inlet chamber communicates at its bottom and an outlet port in said outlet chamber from which moisture may flow by gravity to atmosphere, an annular valve seat at the bottom of said inlet chamber between said inlet and outlet chambers and a resilient hollow disc-like bulb controlling communication between said inlet chamber and said outlet chamber through said valve seat, said disc-like bulb being biased to an expanded position engaging the valve seat and opened by collapsing responsively to a predetermined weight of condensed moisture accumulated thereon.

2. Drain valve means according to claim 1, wherein said disc-like bulb is biased by the differential of the ambient atmosphere pressure and the pressure within the tubing to effect expansion and closing of the valve seat.

3. Drain valve means according to claim 1, wherein said disc-like bulb is an expansible bulb the interior of which is open to ambient atmospheric pressure and the exterior of which seats on and is unseated from said annular valve seat.

4. Drain valve mans according to claim 1, wherein said diaphragm valve means is an expansible bulb the interior of which is pressurized from the tubing and the exterior of which seats on and is unseated from an annular valve seat within which it is also subject to the pressure in the tubing.

5. Drain valve means according to claim 1, wherein said diaphragm valve means is an expansible bulb which seats on and is unseated from an annular valve seat within which it is subject to the pressure in the tubing, and wherein hose means is provided communicating the pressure in the tubing to the interior of said expansible bulb, whereby said valve means is subject differentially to the pressure in the tubing so as to bias said valve means into its seated position on said annular valve seat.

6. For use in a respiratory system having tubing in which the air pressure varies with inhalation and exhalation of the patient, drain valve means for automatically draining condensed moisture from the tubing without admission of ambient atmospheric air into the tubing during inhalation by the patient, said valve means comprising a casing having an outlet chamber and a passage forming an inlet chamber providing communication between the tubing and said chamber, an annular valve seat between said inlet and outlet chambers, said outlet chamber having a drain port through which accumulated moisture may flow to atmosphere, and a resilient expansible disc-like bulb within said outlet chamber seated on and unseated from said annular valve seat to control communication between said passage and said outlet chamber, said diaphragm being biased into seated position on said annular valve seat by the differential between the ambient atmospheric pressure and the pressure within the tubing during the period of inhalation by the patient and unseated from said annular seat during the period of exhalation by the patient by a predetermined weight of moisture accumulated in said passage to which said bulb is subject.

7. A drain valve means according to claim 6, wherein the interior of said bulb is open to ambient atmospheric pressure and the exterior of which is subject when seated on the annular valve seat to the pressure in the tubing.

8. A drain valve means according to claim 6, wherein said diaphragm comprises an expansible bulb the interior of which is subject to the pressure within the tubing and the exterior of which is subject when seated on the annular valve seat to the pressure in the tubing.

9. For use in a respiratory system having tubing through which controlled air under positive pressure is supplied to the patient during inhalation, drain valve means for automatically draining condensed moisture from the tubing without admission of ambient atmospheric air into the tubing during inhalation by the patient, said valve means comprising a casing having an inlet passage communicable with the tubing, a first chamber into which said passage opens, a second chamber having a drain port through which accumulated moisture may flow to atmosphere, and an intermediate passage connecting said first and second chambers, a first and a second bulb-type diaphragm disposed respectively in said first chamber and in said second chamber and connected together such that pressurization of said first chamber causes compression of said first diaphragm resulting in expansion of said second diaphragm, expansion of said second diaphragm effecting biasing thereof into seated relation on an annular valve seat to close communication between said intermediate passage and said second chamber, said second diaphragm being unseated, only during exhalation by the patient, responsive to a predetermined weight of moisture accumulated in said first chamber and intermediate passage to which said second diaphragm is subject, whereby moisture flows to said second chamber and thence by gravity to atmosphere.

10. Drain valve means according to claim 9, wherein check valve means is provided for blocking back flow of air from said first chamber to said inlet passage.

11. Drain valve means according to claim 9, wherein check valve means is interposed in said inlet passage to block flow to the said inlet passage and the tubing by ambient atmospheric air under pressure admitted to said first chamber past said second diaphragm under negative pressure conditions in the tubing.

* * * * *